(12) United States Patent
Yadin

(10) Patent No.: US 7,959,668 B2
(45) Date of Patent: Jun. 14, 2011

(54) BIFURCATED STENT

(75) Inventor: Amnon Yadin, Kfar Vitkin, IL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 539 days.

(21) Appl. No.: 11/653,589

(22) Filed: Jan. 16, 2007

(65) Prior Publication Data
US 2008/0172123 A1    Jul. 17, 2008

(51) Int. Cl.
*A61F 2/06* (2006.01)
(52) U.S. Cl. .................... 623/1.35; 623/1.15
(58) Field of Classification Search .......... 623/1.15, 623/1.35; *A61F 2/06*
See application file for complete search history.

(56) References Cited

U.S. PATENT DOCUMENTS

| | | | |
|---|---|---|---|
| 4,309,994 A | 1/1982 | Grunwald | 128/214 R |
| 4,769,005 A | 9/1988 | Ginsburg et al. | 604/53 |
| 4,774,949 A | 10/1988 | Fogarty | 128/348.1 |
| 4,896,670 A | 1/1990 | Crittenden | 606/194 |
| 4,905,667 A | 3/1990 | Foerster et al. | 128/4 |
| 4,994,071 A | 2/1991 | MacGregor | 606/194 |
| 5,342,387 A | 8/1994 | Summers | 606/198 |
| 5,387,235 A | 2/1995 | Chuter | 623/1 |
| 5,456,712 A | 10/1995 | Maginot | 623/1 |
| 5,476,471 A | 12/1995 | Shifrin et al. | 606/151 |
| 5,591,228 A | 1/1997 | Edoga | 623/1 |
| 5,607,444 A | 3/1997 | Lam | 606/194 |
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |
| 5,632,772 A | 5/1997 | Alcime et al. | 623/1 |

(Continued)

FOREIGN PATENT DOCUMENTS

CA    2220864    7/1999

(Continued)

OTHER PUBLICATIONS

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

(Continued)

*Primary Examiner* — David Isabella
*Assistant Examiner* — Jason-Dennis Stewart
(74) *Attorney, Agent, or Firm* — Vidas, Arrett & Steinkraus, P.A.

(57) ABSTRACT

In at least one embodiment, a stent comprises a plurality of interconnected framework members defining a plurality of cells. A portion of the interconnected framework members comprise a side branch structure defining an inner side branch cell that is shaped differently than other cells of the stent. The side branch structure comprises a first serpentine ring extending around the inner side branch cell. The first serpentine ring comprises alternating inner turns and outer turns connected by straight struts. The inner turns are distributed around a reference circle centered upon a side branch center point. The side branch structure further comprises a second serpentine ring extending around the first serpentine ring. The second serpentine ring comprises alternating inner turns and outer turns connected by straight struts. The second serpentine ring has the same number of inner turns and outer turns as the first serpentine ring. The side branch structure further comprises a plurality of inner side branch connectors, each inner side branch connector spanning between the first serpentine ring and the second serpentine ring in a side branch radial direction.

14 Claims, 12 Drawing Sheets

U.S. PATENT DOCUMENTS

| | | | |
|---|---|---|---|
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |
| 5,697,971 A | 12/1997 | Fischell et al. | 623/1 |
| 5,709,713 A | 1/1998 | Evans et al. | 623/1 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,755,773 A | 5/1998 | Evans et al. | 623/1 |
| 5,755,778 A | 5/1998 | Kleshinski | 623/1 |
| 5,782,906 A | 7/1998 | Marshall et al. | 623/1 |
| 5,824,036 A | 10/1998 | Lauterjung | 623/1 |
| 5,824,040 A | 10/1998 | Cox et al. | 623/1 |
| 5,827,320 A | 10/1998 | Richter et al. | 606/194 |
| 5,851,464 A | 12/1998 | Davila et al. | 264/103 |
| 5,868,777 A | 2/1999 | Lam | 606/194 |
| 5,893,887 A | 4/1999 | Jayaraman | 623/1 |
| 5,961,548 A | 10/1999 | Shmulewitz | 623/1 |
| 5,972,017 A | 10/1999 | Berg et al. | 606/198 |
| 6,013,054 A | 1/2000 | Jiun Yan | 604/96 |
| 6,017,324 A | 1/2000 | Tu et al. | 604/96 |
| 6,017,363 A | 1/2000 | Hojeibane | 623/1 |
| 6,030,414 A | 2/2000 | Taheri | 623/1 |
| 6,033,434 A | 3/2000 | Borghi | 623/1 |
| 6,033,435 A | 3/2000 | Penn et al. | 623/1 |
| 6,056,775 A | 5/2000 | Borghi et al. | 623/1.16 |
| 6,059,824 A | 5/2000 | Taheri | 623/1 |
| 6,068,655 A | 5/2000 | Seguin et al. | 623/1 |
| 6,086,611 A | 7/2000 | Duffy et al. | 623/1 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,129,738 A | 10/2000 | Lashinski et al. | 606/194 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,183,509 B1 | 2/2001 | Dibie | 623/1.35 |
| 6,203,568 B1 | 3/2001 | Lombardi et al. | 623/1.13 |
| 6,210,380 B1 | 4/2001 | Mauch | 604/284 |
| 6,210,429 B1 | 4/2001 | Vardi et al. | 623/1.11 |
| 6,210,433 B1 | 4/2001 | Larre | 623/1.15 |
| 6,254,593 B1 | 7/2001 | Wilson | 606/1.11 |
| 6,258,115 B1 | 7/2001 | Dubrul | 606/200 |
| 6,258,116 B1 | 7/2001 | Hojeibane | 623/1.16 |
| 6,261,305 B1 | 7/2001 | Marotta et al. | 606/194 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,290,673 B1 | 9/2001 | Shanley | 604/102.02 |
| 6,325,822 B1 | 12/2001 | Chouinard et al. | 623/1.35 |
| 6,325,826 B1 | 12/2001 | Vardi et al. | 623/1.35 |
| 6,334,864 B1 | 1/2002 | Amplatz et al. | 606/200 |
| 6,346,089 B1 | 2/2002 | Dibie | 603/1.15 |
| 6,355,060 B1 | 3/2002 | Lenker et al. | 623/1.34 |
| 6,361,544 B1 | 3/2002 | Wilson et al. | 606/194 |
| 6,361,555 B1 | 3/2002 | Wilson | 623/1.11 |
| 6,383,213 B2 | 5/2002 | Wilson et al. | 623/1.11 |
| 6,395,018 B1 | 5/2002 | Castaneda | 623/1.13 |
| 6,436,104 B2 | 8/2002 | Hojeibane | 606/108 |
| 6,436,134 B2 | 8/2002 | Richter et al. | 623/1.15 |
| 6,508,836 B2 | 1/2003 | Wilson et al. | 623/1.35 |
| 6,517,558 B2 | 2/2003 | Gittings et al. | 606/153 |
| 6,520,988 B1 | 2/2003 | Colombo et al. | 623/1.35 |
| 6,540,779 B2 | 4/2003 | Richter et al. | 623/1.35 |
| 6,579,309 B1 | 6/2003 | Loos et al. | 623/1.16 |
| 6,579,312 B2 | 6/2003 | Wilson et al. | 623/1.35 |
| 6,582,394 B1 | 6/2003 | Reiss et al. | 604/96.01 |
| 6,596,020 B2 | 7/2003 | Vardi et al. | 623/1.11 |
| 6,599,316 B2 | 7/2003 | Vardi et al. | 623/1.15 |
| 6,645,242 B1 | 11/2003 | Quinn | 623/1.16 |
| 6,689,156 B1 | 2/2004 | Davidson et al. | 623/1.11 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,749,628 B1 | 6/2004 | Cho et al. | 623/1.15 |
| 6,776,793 B2 | 8/2004 | Brown et al. | 623/1.15 |
| 6,811,566 B1 | 11/2004 | Penn et al. | 623/1.15 |
| 6,835,203 B1 | 12/2004 | Vardi et al. | 623/1.34 |
| 6,858,038 B2 | 2/2005 | Heuser | 623/1.35 |
| 6,884,258 B2 | 4/2005 | Vardi et al. | 623/1.11 |
| 6,896,699 B2 | 5/2005 | Wilson et al. | 623/1.35 |
| 6,932,837 B2 | 8/2005 | Amplatz et al. | 623/1.15 |
| 6,955,687 B2 | 10/2005 | Richter et al. | 623/1.35 |
| 6,955,688 B2 | 10/2005 | Wilson et al. | 623/1.35 |
| 6,962,602 B2 | 11/2005 | Vardi et al. | 623/1.11 |
| 7,018,400 B2 | 3/2006 | Lashinski et al. | 623/1.11 |
| 7,060,091 B2 | 6/2006 | Killion et al. | 623/1.15 |
| 2001/0003161 A1 | 6/2001 | Vardi et al. | 623/1.11 |
| 2001/0004706 A1 | 6/2001 | Hojeibane | 623/1.11 |
| 2001/0004707 A1 | 6/2001 | Dereume et al. | 623/1.16 |
| 2001/0012927 A1 | 8/2001 | Mauch | 604/284 |
| 2001/0016766 A1 | 8/2001 | Vardi et al. | 623/1.11 |
| 2001/0016767 A1 | 8/2001 | Wilson et al. | 623/1.11 |
| 2001/0016768 A1 | 8/2001 | Wilson et al. | 623/1.11 |
| 2001/0025195 A1 | 9/2001 | Shaolian et al. | 623/1.13 |
| 2001/0027291 A1 | 10/2001 | Shanley | 604/104 |
| 2001/0027338 A1 | 10/2001 | Greenberg | 623/1.13 |
| 2001/0029396 A1 | 10/2001 | Wilson et al. | 623/1.11 |
| 2001/0037116 A1 | 11/2001 | Wilson et al. | 606/108 |
| 2001/0037138 A1 | 11/2001 | Wilson et al. | 623/1.11 |
| 2001/0039448 A1 | 11/2001 | Dibie | 623/1.16 |
| 2001/0049552 A1 | 12/2001 | Richter et al. | 623/1.15 |
| 2001/0056297 A1 | 12/2001 | Hojeibane | 623/1.16 |
| 2002/0013618 A1 | 1/2002 | Marotta et al. | 623/1.15 |
| 2002/0013619 A1 | 1/2002 | Shanley | 623/1.15 |
| 2002/0022874 A1 | 2/2002 | Wilson | 623/1.11 |
| 2002/0026232 A1 | 2/2002 | Marotta et al. | 623/1.16 |
| 2002/0035392 A1 | 3/2002 | Wilson | 623/1.11 |
| 2002/0042650 A1 | 4/2002 | Vardi et al. | 623/1.35 |
| 2002/0052648 A1 | 5/2002 | McGuckin, Jr. et al. | 623/1.35 |
| 2002/0072790 A1 | 6/2002 | McGuckin, Jr. et al. | 623/1.12 |
| 2002/0111675 A1 | 8/2002 | Wilson | 623/1.35 |
| 2002/0156516 A1 | 10/2002 | Vardi et al. | 623/1.11 |
| 2002/0156517 A1 | 10/2002 | Perouse | 623/1.11 |
| 2002/0165604 A1 | 11/2002 | Shanley | 623/1.15 |
| 2002/0173835 A1 | 11/2002 | Bourang et al. | 623/1.11 |
| 2002/0173840 A1 | 11/2002 | Brucker et al. | 623/1.16 |
| 2002/0183763 A1 | 12/2002 | Callol et al. | 606/108 |
| 2002/0193872 A1 | 12/2002 | Trout, III et al. | 623/1.34 |
| 2002/0193873 A1 | 12/2002 | Brucker et al. | 623/1.35 |
| 2003/0009209 A1 | 1/2003 | Hojeibane | 623/1.11 |
| 2003/0028233 A1 | 2/2003 | Vardi et al. | 623/1.11 |
| 2003/0050688 A1 | 3/2003 | Fischell et al. | 623/1.15 |
| 2003/0055483 A1 | 3/2003 | Gumm | 623/1.11 |
| 2003/0074047 A1 | 4/2003 | Richter | 623/1.11 |
| 2003/0093109 A1 | 5/2003 | Mauch | 606/194 |
| 2003/0097169 A1 | 5/2003 | Brucker et al. | 623/1.11 |
| 2003/0114912 A1 | 6/2003 | Sequin et al. | 623/1.11 |
| 2003/0125791 A1 | 7/2003 | Sequin et al. | 623/1.11 |
| 2003/0125802 A1 | 7/2003 | Callol et al. | 623/1.35 |
| 2003/0135259 A1 | 7/2003 | Simso | 623/1.12 |
| 2003/0181923 A1 | 9/2003 | Vardi | 606/108 |
| 2003/0195606 A1 | 10/2003 | Davidson et al. | 623/1.11 |
| 2004/0006381 A1 | 1/2004 | Sequin et al. | 623/1.12 |
| 2004/0015227 A1 | 1/2004 | Vardi et al. | 623/1.16 |
| 2004/0044396 A1 | 3/2004 | Clerc et al. | 623/1.13 |
| 2004/0059406 A1 | 3/2004 | Cully et al. | 623/1.11 |
| 2004/0088007 A1 | 5/2004 | Eidenschink | 607/1 |
| 2004/0117003 A1 | 6/2004 | Ouriel et al. | 623/1.35 |
| 2004/0133268 A1 | 7/2004 | Davidson et al. | 623/1.35 |
| 2004/0138732 A1 | 7/2004 | Suhr et al. | 623/1.11 |
| 2004/0138737 A1 | 7/2004 | Davidson et al. | 623/1.35 |
| 2004/0148006 A1 | 7/2004 | Davidson et al. | 623/1.11 |
| 2004/0172121 A1 | 9/2004 | Eidenschink et al. | 623/1.11 |
| 2004/0186560 A1 | 9/2004 | Alt | 623/1.35 |
| 2004/0225345 A1 | 11/2004 | Fischell et al. | 623/1.11 |
| 2004/0267352 A1 | 12/2004 | Davidson et al. | 623/1.15 |
| 2005/0010278 A1 | 1/2005 | Vardi et al. | 623/1.35 |

| 2005/0015108 | A1 | 1/2005 | Williams et al. | 606/194 |
| 2005/0060027 | A1 | 3/2005 | Khenansho et al. | 623/1.35 |
| 2005/0102021 | A1 | 5/2005 | Osborne | 623/1.13 |
| 2005/0102023 | A1 | 5/2005 | Yadin et al. | 623/1.15 |
| 2005/0119731 | A1 | 6/2005 | Brucker et al. | 623/1.35 |
| 2005/0131526 | A1 | 6/2005 | Wong | 623/1.15 |
| 2005/0149161 | A1 | 7/2005 | Eidenschink et al. | 623/1.11 |
| 2005/0154442 | A1 | 7/2005 | Eidenschink et al. | 623/1.11 |
| 2005/0154444 | A1 | 7/2005 | Quadri | 623/1.13 |
| 2005/0183259 | A1 | 8/2005 | Eidenschink et al. | 29/508 |
| 2005/0209673 | A1 | 9/2005 | Shaked | 623/1.11 |
| 2005/0228483 | A1 | 10/2005 | Kaplan et al. | 623/1.15 |
| 2006/0036315 | A1 | 2/2006 | Yadin et al. | 623/1.35 |
| 2006/0041303 | A1 | 2/2006 | Israel | 623/1.11 |
| 2006/0079956 | A1 | 4/2006 | Eigler et al. | 623/1.35 |
| 2006/0173528 | A1 | 8/2006 | Feld et al. | 623/1.15 |

FOREIGN PATENT DOCUMENTS

| DE | 9014845 | 2/1991 |
| DE | 29701758 | 3/1997 |
| DE | 29701883 | 5/1997 |
| EP | 0479730 | 10/1991 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 0897700 | 7/2002 |
| EP | 0684022 | 2/2004 |
| EP | 1157674 | 7/2005 |
| EP | 1031330 | 11/2005 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/36709 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15109 | 4/1999 |
| WO | 99/24104 | 5/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 01/45594 | 6/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71055 | 11/2000 |
| WO | 00/74595 | 12/2000 |
| WO | 01/21095 | 3/2001 |
| WO | 01/21109 | 3/2001 |
| WO | 01/21244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/068012 | 9/2002 |
| WO | 03/055414 | 7/2003 |
| WO | 2004/026180 | 4/2004 |
| WO | 2005/009295 | 2/2005 |
| WO | 2005/014077 | 2/2005 |
| WO | 2005122959 | 12/2005 |
| WO | 2007102961 | 9/2007 |

OTHER PUBLICATIONS

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

Caputo, Ronald P., "Stent Jail: A Minimum-Security Prison," *The American Journal of Cardiology*, vol. 77, pp. 1226-1230 (Jun. 1, 1996).

Colombo, M.D., Antonio, ""Kissing" Stent for Bifurcational Coronary Lesion," *Catheterization and Cardiovascular Diagnosis*, vol. 30, pp. 327-330 (Dec. 1993).

Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: To Treat or Not to Treat," *Catheterization and Cardiovascular Interventions*, vol. 50, pp. 411-412 (2000).

U.S. Appl. No. 09/663,111, filed Sep. 15, 2000, Davidson et al.
U.S. Appl. No. 09/614,472, filed Jul. 11, 2000, Davidson et al.
U.S. Appl. No. 09/325,996, filed Jun. 4, 1999, Vardi et al.

BIFURCATED STENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Stents, grafts, stent-grafts, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents can be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

There remains a need for novel stent designs that are suitable for use at a vessel bifurcation.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a stent comprises a plurality of interconnected framework members defining a plurality of cells. A portion of the interconnected framework members comprise a side branch structure defining an inner side branch cell that is shaped differently than other cells of the stent. The side branch structure comprises a first serpentine ring extending around the inner side branch cell. The first serpentine ring comprises alternating inner turns and outer turns connected by straight struts. The inner turns are distributed around a reference circle centered upon a side branch center point. The side branch structure further comprises a second serpentine ring extending around the first serpentine ring. The second serpentine ring comprises alternating inner turns and outer turns connected by straight struts. The second serpentine ring has the same number of inner turns and outer turns as the first serpentine ring. The side branch structure further comprises a plurality of inner side branch connectors, each inner side branch connector spanning between the first serpentine ring and the second serpentine ring in a side branch radial direction.

In at least one embodiment, a stent comprises a plurality of interconnected framework members defining a plurality of cells. A portion of the interconnected framework members comprise a side branch structure defining an inner side branch cell that is shaped differently than other cells of the stent. The side branch structure comprises a plurality of arcuate struts aligned along a first reference circle centered upon a side branch center point. The plurality of arcuate struts collectively comprises at least half of a circumference of the first reference circle.

In at least one embodiment, a stent comprises a plurality of interconnected framework members defining a plurality of cells. A portion of the interconnected framework members comprise a side branch structure defining an inner side branch cell that is shaped differently than other cells of the stent. The side branch structure comprises a serpentine ring extending around the inner side branch cell. The serpentine ring comprises alternating inner turns and outer turns connected by straight struts. The inner turns comprise first inner turns and second inner turns. Each first inner turn comprises a central angle that is greater than 180 degrees.

In at least one embodiment, a stent comprises a plurality of interconnected framework members defining a plurality of cells. A portion of the interconnected framework members comprise a side branch structure defining an inner side branch cell that is shaped differently than other cells of the stent. The side branch structure comprises a serpentine ring extending around the inner side branch cell. The serpentine ring comprises alternating petals and linking members. Each linking member comprises a plurality of parallel struts connected by turns.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
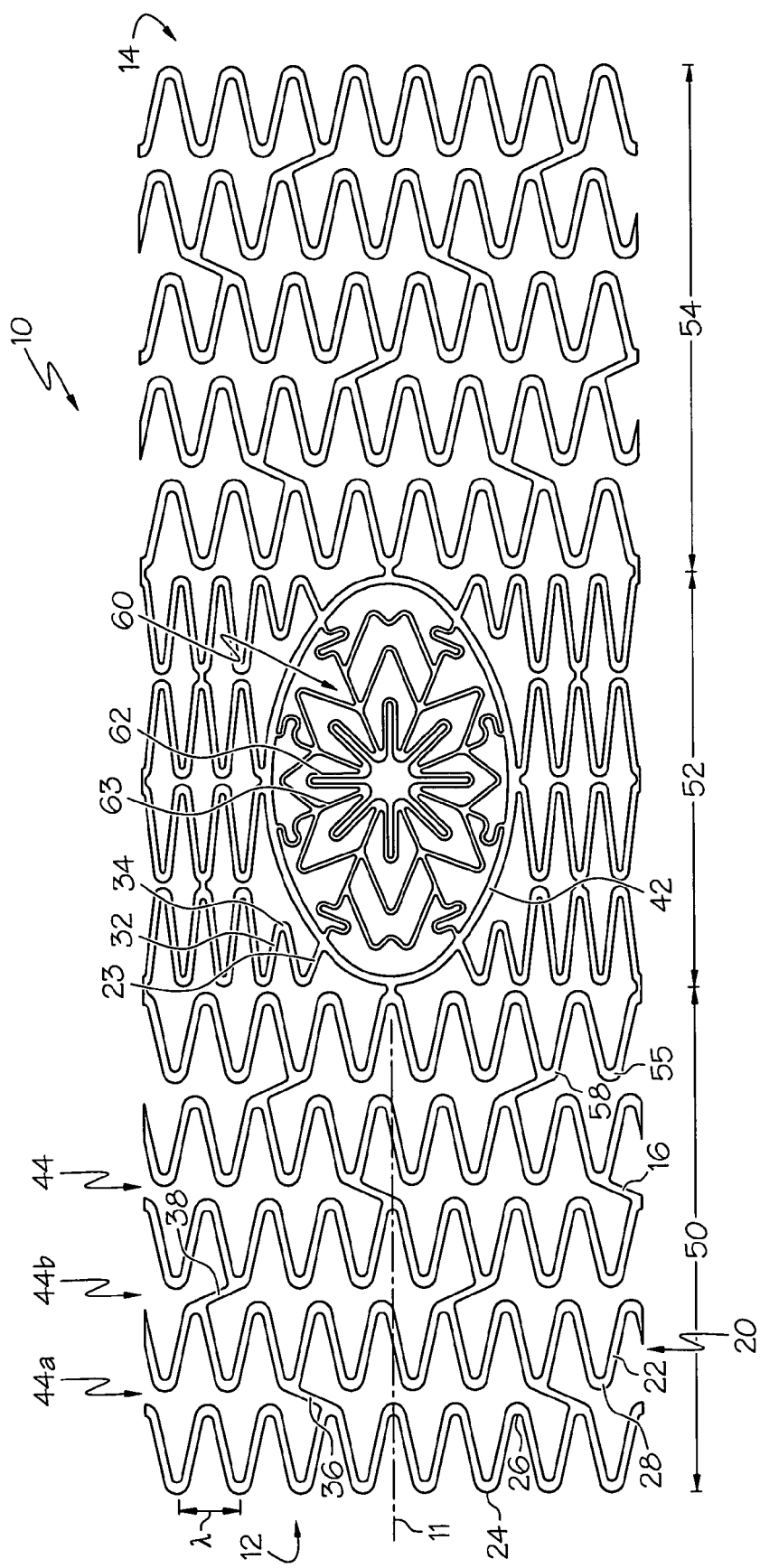
FIG. 1 shows a flat pattern for an embodiment of a stent.

While this invention may be embodied in many different forms, there are described in detail herein specific embodiments of the invention. This description is an exemplification of the principles of the invention and is not intended to limit the invention to the particular embodiments illustrated.

FIGS. 1, 6, 7, 9, 10 and 12 each show a flat pattern for an embodiment of a stent 10 having a proximal end 12, a distal end 14 and a plurality of serpentine bands 20. For the purposes of this disclosure, like reference numerals in the figures shall refer to like features unless otherwise indicated.

In some embodiments, each serpentine band 20 comprises a plurality of struts 22. Circumferentially adjacent struts 22 within a serpentine band 20 are connected by turns 28. Turns 28 that point toward the proximal end 12 of the stent 10 comprise proximal peaks 24, and turns 28 that point toward the distal end 14 of the stent 10 comprise distal valleys 26. Each serpentine band 20 extends about at least a portion of the circumference of the stent 10.

A stent 10 can have any suitable number of serpentine bands 20. In various embodiments, a serpentine band 20 can have any suitable number of struts 22 and any suitable number of turns 28. In some embodiments, a serpentine band 20 can have a constant wavelength $\lambda$ or distance between repeating elements of the serpentine band 20. For example, a wavelength $\lambda$ may comprise a distance between adjacent proximal peaks 24 of a serpentine band 20, or a distance between adjacent distal valleys 26 of a serpentine band 20. In some embodiments, the wavelength $\lambda$ can change between adjacent serpentine bands 20. For example, the wavelength $\lambda$ of various serpentine bands 20 may be the shortest for serpentine bands 20 located near the center of the stent 10, and may increase as the stent 10 is traversed toward either end 12, 14. In some embodiments, a serpentine band 20 may have multiple portions, where each portion comprises a different wavelength $\lambda$.

A serpentine band 20 can span any suitable distance along the length of the stent 10. In some embodiments, the proximal peaks 24 of a given serpentine band 20 can be aligned about a circumference of the stent 10, and the distal valleys 26 can be similarly aligned about another circumference of the stent 10. In some embodiments, various peaks 24 may be offset from other peaks 24 within a given serpentine band 20, and various valleys 26 may be offset from other valleys 26 within the band 20.

Each strut 22 comprises a width, which can be measured in a direction normal to the length of the strut 22. In some embodiments, all struts 22 within a given serpentine band 20 have the same width. In some embodiments, the width of various struts 22 within a serpentine band 20 can change. In some embodiments, the width of struts 22 of one serpentine band 20 can be different from the width of struts 22 of another serpentine band 20.

Each turn 28 has a width, which can be measured in a direction normal to the side of the turn 28 (i.e. normal to a tangent line). In some embodiments, the width of a turn 28 can be greater than the width of one or more struts 22 of the stent 10. In some embodiments, the width of a turn 28 may be less than the width of one or more struts 22 of the stent 10. In some embodiments, the width of a turn 28 may vary from one end of the turn 28 to the other. For example, a turn 28 may connect to a strut 22 at one end having the same width as the strut 22. The width of the turn 28 may increase, and in some embodiments may reach a maximum at a midpoint of the turn 28. The width of the turn 28 may then decrease to the width of another strut 22, which may be connected to the second end of the turn 28.

In some embodiments, for example as shown in FIGS. 1, 6, 7, 9, 10 and 12, serpentine bands 20 that are adjacent to one another along the length of the stent 10 are connected by at least one connector strut 16. In some embodiments, a connector strut 16 spans between turns 28 of adjacent serpentine bands 20. For example, one end of a connector strut 16 can connect to a distal valley 26 of one serpentine band 20, and the other end of the connector strut 16 can connect to a proximal peak 24 of an adjacent serpentine band 20.

Connector struts 16 can connect to any portion of a serpentine band 20, such as a turn 28, or in some embodiments, a strut 22. In some embodiments, a connector strut 16 is linear or straight along its length. In some embodiments, a connector strut 16 can include curvature along its length, can further include multiple portions of curvature, for example a convex portion and a concave portion that may be connected at an inflection point.

In some embodiments, a stent 10 comprises a first type of connector strut 36 and a second type of connector strut 38. A first connector strut 36 may extend in a first direction. The first connector strut 36 may be oriented at a first angle to a stent lengthwise axis 11. A second connector strut 38 may extend in a second direction that is different than or non-parallel to the first direction. In some embodiments, the first angle and the second angle may have the same magnitude but different orientations. For example, a first connector strut 36 may form a 70° angle with a stent lengthwise axis 11, while a second connector strut 38 may form a negative 70° angle with the stent lengthwise axis 11. In some embodiments, a first angle may comprise a mirror image of a second angle across a line parallel to the stent lengthwise axis 11.

A stent 10 further comprises a plurality of cells 30. A cell 30 comprises an opening in the stent 10 between the structural framework elements, such as serpentine bands 20 and connector struts 16. In some embodiments, a cell 30 may be bounded by a serpentine band 20, a connector strut 16, another serpentine band 20 and another connector strut 16.

In some embodiments, for example as shown in FIGS. 1, 6, 7, 9, 10 and 12, a stent 10 comprises a first end region 50, a central region 52 and a second end region 54. Each region 50, 52, 54 extends across a portion of the length of the stent 10. Each region 50, 52, 54 includes a plurality structural framework elements, for example a plurality of serpentine bands 20. In some embodiments, all of the serpentine bands 20 within a given region 50, 52, 54 are similar in size and shape. In some embodiments, various serpentine bands 20 within a given region 50, 52, 54 may be different in size, shape, strut width, wavelength $\lambda$, etc. For example, in some embodiments, serpentine bands 20 located in the central region 52 span a greater distance along the length of the stent 10 than serpentine bands 20 located in the end regions 50, 54. In some embodiments, the struts 22 of serpentine bands 20 located in the central region 52 have a greater length than struts 22 located in the end regions 50, 54. In some embodiments, the struts 22 of serpentine bands 20 located in the end regions 50, 54 are wider than struts 22 located in the central region 52. In some embodiments, the wavelength λ of serpentine bands 20 located in the central region 52 is less than the wavelength λ of serpentine bands 20 located in the end regions 50, 54.

In some embodiments, an area of the stent 10 located between two adjacent serpentine bands 20 can be considered a connector column 44. Each connector column 44 comprises a plurality of connector struts 16. In some embodiments, each connector strut 16 in a connector column 44 can be similar to one another. For example, each connector strut 16 in a first connector column 44a can comprise a first type of connector strut 36. Each connector strut 16 in a second connector column 44b can comprise a second type of connector strut 38.

In some embodiments, first connector columns 44a and second connector columns 44b can alternate along the length of the stent 10. Thus, each interior serpentine band 20 can be positioned between a first connector column 44a and a second connector column 44b. Accordingly, connector struts 16 that connect to one side of a serpentine band 20 can comprise first connector struts 36, and connector struts 16 that connect to the other side of the serpentine band 20 can comprise second connector struts 38.

Turns 28 can comprise connected turns 58 or unconnected turns 55 depending upon whether the turn 28 connects to a connector strut 16.

A serpentine band 20 can have more unconnected turns 55 than connected turns 58. In some embodiments, a serpentine band 20 has three unconnected turns 55 for each connected turn 58. The 3:1 ratio of unconnected turns 55 to connected turns 58 can also apply to the proximal peaks 24 and to the distal valleys 26.

In some embodiments, for example as shown in FIGS. 1, 2 6-12, the central region 52 further comprises a side branch structure 60 and a side branch support ring 42. In some embodiments, the support ring 42 can be considered a portion of the side branch structure 60. In various embodiments, some or all of the serpentine bands 20 located in the central region 52 extend about a portion of the stent circumference, while the remainder of the circumference is occupied by the side branch structure 60 and the support ring 42.

In some embodiments, serpentine bands 20 located in the central region 52 attach directly to a portion of the support ring 42.

In some embodiments, a serpentine band 20 comprises one or more shorter struts 32. A shorter strut 32 is generally shorter than other struts 22 of the serpentine band 20. Shorter struts 32 can be located in proximity to the side branch structure 60, and in some embodiments, a shorter strut 32 can connect to a portion of the side branch structure 60. A serpentine band 20 can also comprise one or more offset turns 34, which can connect to one or more shorter struts 32. An offset turn 34 is generally offset from other turns 28 of the serpentine band 20 that face the same direction (e.g. point toward the same direction). For example, most of the distal valleys 26 of a serpentine band 20 may be aligned about a reference circumference of the stent 10, while an offset distal valley 34 located in the same serpentine band 20 is not aligned on the aforementioned reference circumference.

In some embodiments, a serpentine band 20 can comprise one or more nonparallel struts 23, wherein the nonparallel strut 23 is not parallel to any other struts 22 of the serpentine band 20 when viewed as a flat pattern.

In various embodiments, serpentine bands 20 located in the central region 52 can comprise any suitable combination of struts 22 and turns 28, including struts of varying length, struts having curvature and turns having any suitable location and orientation.

The side branch structure 60 comprises structural elements that can displace outwardly from other portions of the stent 10, for example extending into a side branch vessel. The side branch structure 60 generally comprises a plurality of serpentine rings 62 and a plurality of side branch connectors 63.

Figure 2:
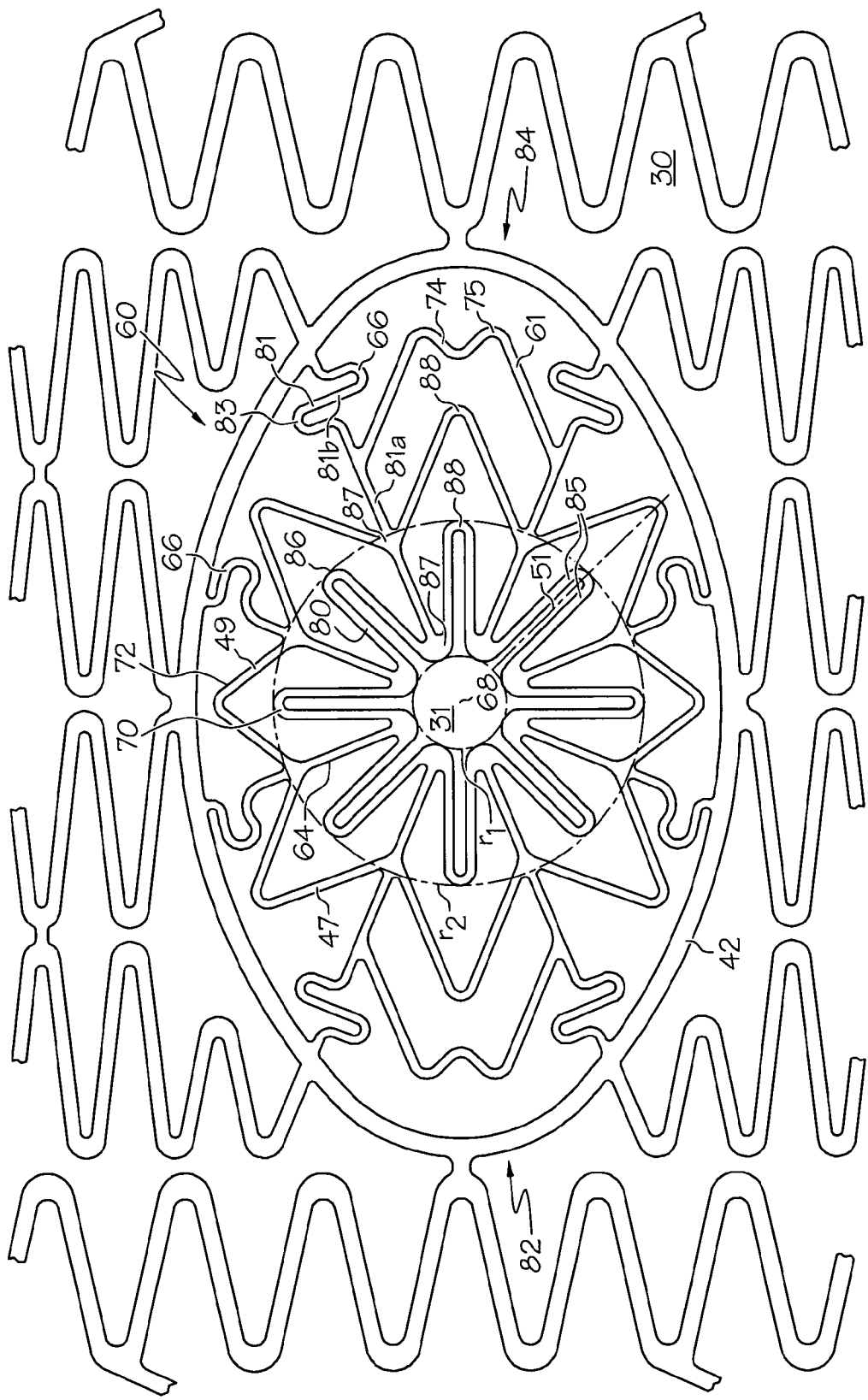
FIG. 2 shows a portion of FIG. 1 in greater detail.

FIG. 2 shows the side branch structure 60 from the embodiment of FIG. 1 in greater detail.

In some embodiments, the side branch structure 60 comprises a first serpentine ring 70, a second serpentine ring 72 and plurality of side branch inner connectors 64. The serpentine rings 70, 72 are also referred to herein as side branch rings.

The first serpentine ring 70 extends around and defines an inner side branch cell 31. The inner side branch cell 31 can be shaped differently from all other cells 30 of the stent 10. A side branch center point 68 comprises the center of the inner side branch cell 31. In some embodiments, the side branch rings 70, 72 are centered upon the side branch center point 68.

In some embodiments, the first serpentine ring 70 comprises a plurality of alternating struts 80 and turns 86. In some embodiments, each strut 80 is straight along its length. In some embodiments, each strut 80 of the first serpentine ring 70 has the same length. In some embodiments, the first serpentine ring 70 comprises a plurality of strut pairs 85. Each strut pair 85 comprises two struts 80, wherein the struts 80 of the pair 85 are mirror images of one another taken across a side branch radial line 51, such as a side branch radial line 51 that bisects a turn 86 of a serpentine ring 62. In some embodiments, the struts 80 of a pair 85 are parallel to one another and parallel to the side branch radial line 51. In some embodiments, the struts 80 of a strut pair 85 are connected by a turn 86, such as an outer turn 88 as described below.

In some embodiments, a turn 86 can be centered in a side branch radial direction. Thus, a line oriented in a side branch radial direction that passes through the side branch center point 68 can bisect a turn 86. When a turn 86 is bisected by a line, a first half of the turn located on one side of the line comprises a mirror image of a second half of the turn located on the other side of the line.

In some embodiments, the turns 86 of the first serpentine ring 70 comprise alternating inner turns 87 and outer turns 88. Thus, the turns 86 located on either side of an inner turn 87 comprise outer turns 88, and the turns 86 located on either side of an outer turn 88 comprise inner turns 87. The inner turns 87 are generally located closer to the side branch center point 68 than the outer turns 88. In some embodiments, inner turns 87 point inward with respect to the side branch, for example pointing toward the side branch center point 68. In some embodiments, outer turns 88 point outward with respect to the side branch, for example pointing away from the side branch center point 68.

In some embodiments, each inner turn 87 of the first serpentine ring 70 comprises the same shape and has the same radius of curvature as all other inner turns 87 of the first serpentine ring 70. In some embodiments, each outer turn 88 of the first serpentine ring 70 comprises the same shape and has the same radius of curvature as all other outer turns 88 of the first serpentine ring 70.

In some embodiments, the inner turns 87 of the first serpentine ring 70 are each located an equal distance away from the side branch center point 68, and thus can be considered aligned around a first reference circle $r_1$ centered upon the side branch center point 68. In some embodiments, the inner turns 87 of the first serpentine ring 70 are equally spaced around the first reference circle $r_1$.

In some embodiments, the outer turns 88 of the first serpentine ring 70 are each located an equal distance away from the side branch center point 68, and thus can be considered aligned around a second reference circle $r_2$ centered upon the side branch center point 68. In some embodiments, the outer turns 88 of the first serpentine ring 70 are equally spaced around the second reference circle $r_2$.

The second serpentine ring 72 extends around the first serpentine ring 70. In some embodiments, the second serpentine ring 72 is coaxial with the first serpentine ring 70, and thus can be centered upon the side branch center point 68.

In some embodiments, the second serpentine ring 72 comprises a plurality of alternating struts 80 and turns 86. In some embodiments, each strut 80 is straight along its length. In some embodiments, the second serpentine ring 72 comprises first struts 47 and second struts 49, wherein the first struts 47 are longer than the second struts 49. In some embodiments, multiple first struts 47 can be connected by a turn 86. In some embodiments, multiple second struts 49 can be connected by a turn 86. In various embodiments, struts 80 of the second serpentine ring 72 can be longer and/or shorter than struts 80 of the first serpentine ring 70. In some embodiments, first struts 47 of the second serpentine ring 72 are longer than one or more struts 80 of the first serpentine ring 70, and second struts 49 of the second serpentine ring 72 are shorter than one or more struts 80 of the first serpentine ring 70. In some embodiments, each strut 80 of the second serpentine ring 72 can have the same length.

In some embodiments, the turns 86 of the second serpentine ring 72 comprise alternating inner turns 87 and outer turns 88. Thus, the turns 86 located on either side of an inner turn 87 comprise outer turns 88, and the turns 86 located on either side of an outer turn 88 comprise inner turns 87. The inner turns 87 are generally located closer to the side branch center point 68 than the outer turns 88. In some embodiments, inner turns 87 point inward with respect to the side branch, for example pointing toward the side branch center point 68. In some embodiments, outer turns 88 point outward with respect to the side branch, for example pointing away from the side branch center point 68.

In some embodiments, the second serpentine ring 72 can comprise the same number of struts 80 and turns 86 as the first serpentine ring 70. In some embodiments, the second serpentine ring 72 can comprise the same number of inner turns 87 and outer turns 88 as the first serpentine ring 70.

In some embodiments, the second serpentine ring 72 can be symmetrical across a side branch major axis that extends parallel to the stent longitudinal axis 11. In some embodiments, the second serpentine ring 72 can be symmetrical across a side branch minor axis that extends perpendicular to the stent longitudinal axis 11.

In some embodiments, a turn 86 of the second serpentine ring 72 can be centered in a side branch radial direction. Thus, a line oriented in a side branch radial direction 51 that passes through the side branch center point 68 can bisect a turn 86.

In some embodiments, a turn 86 of the second serpentine ring 72 can be aligned with a turn 86 of the first serpentine ring 70 in a side branch radial direction. Thus, a line oriented in a side branch radial direction that bisects a turn 86 of the first serpentine ring 70 can also bisect a turn 86 of the second serpentine ring 72. In some embodiments, an inner turn 87 of the second serpentine ring 72 can be aligned with an inner turn 87 of the first serpentine ring 70 in a side branch radial direction. In some embodiments, an outer turn 88 of the second serpentine ring 72 can be aligned with an outer turn 88 of the first serpentine ring 70 in a side branch radial direction. In some embodiments, each inner turn 87 of the second serpentine ring 72 is aligned with an inner turn 87 of the first serpentine ring 70 in a side branch radial direction, and each outer turn 88 of the second serpentine ring 72 is aligned with an outer turn 88 of the first serpentine ring 70 in a side branch radial direction.

In some embodiments, each inner turn 87 of the second serpentine ring 72 comprises the same shape and has the same radius of curvature as all other inner turns 87 of the second serpentine ring 72. In some embodiments, the inner turns 87 of the second serpentine ring 72 are each located an equal distance away from the side branch center point 68, and thus can be considered aligned around a third reference circle (not shown) centered upon the side branch center point 68. In some embodiments, the inner turns 87 of the second serpentine ring 72 are equally spaced around the third reference circle. In some embodiments, the third reference circle comprises a smaller radius than the second reference circle $r_2$, and thus at least a portion of each outer turn 88 of the first serpentine ring 70 can be located farther away from the side branch center point 68 than at least a portion of each inner turn 87 of the second serpentine ring 72.

In some embodiments, some of the outer turns 88 of the second serpentine ring 72 can be located farther away from the side branch center point 68 than other outer turns 88 of the second serpentine ring 72.

In some embodiments, an inner connector 64 connects between the first serpentine ring 70 and the second serpentine ring 72. In some embodiments, an inner connector 64 is connected at an inner end to a turn 86 of the first side branch ring 70 and is connected at an outer end to a turn 86 of the second side branch ring 72. In some embodiments, an inner connector 64 spans between an inner turn 87 of the first serpentine ring 70 and an inner turn 87 of the second serpentine ring 72.

In some embodiments, an inner connector 64 is straight along its length and is oriented in a side branch radial direction. In some embodiments, one inner connector 64 and another inner connector 64 that is located across the inner side branch cell 31 are both oriented upon a common reference line that passes through the side branch center point 68. In some embodiments, all of the inner connectors 64 are evenly distributed around the side branch center point 68.

In some embodiments, the number of inner connectors 64 is equal to the number of inner turns 87 of the first serpentine ring 70.

In some embodiments, the side branch structure 60 further comprises one or more side branch outer connectors 66. In some embodiments, a side branch outer connector 66 is connected at one end to the second serpentine ring 72 and is connected at the other end to another portion of the stent 10, such as a support ring 42 that extends around the side branch structure 60. In some embodiments, each inner turn 87 of the second serpentine ring 72 is connected to a side branch outer connector 66.

In some embodiments, an outer connector 66 comprises struts 81 and turns 83. Each strut 81 can be straight along its length. Some outer connectors 66 can comprise more struts 81 and turns 83 than other outer connectors 66. In some embodiments, an outer connector 66 can comprise at least one strut 81*a* oriented in a side branch radial direction, and at least one strut 81*b* oriented perpendicular to a side branch radial direction. In some embodiments, an outer connector 66 can include a plurality of struts 81b that are oriented perpendicular to a side branch radial direction.

In some embodiments, a stent 10 can comprise an ancillary side branch structure 61, which can often be located near the proximal and/or distal end(s) of the side branch structure 60. In some embodiment, ancillary side branch structure 61 can comprise ancillary struts 74 and ancillary turns 75. In some embodiments, a continuous ancillary side branch structure 61 can be attached at one end to a side branch outer connector 66, and can be attached at the other end to another side branch outer connector 66. In some embodiments, the ancillary side branch structure 61 can be considered a portion of the side branch structure 60.

In some embodiments, the support ring 42 extends around the side branch structure 60 and provides a more rigid support to the side branch structure 60 than would otherwise be provided by the serpentine bands 20 alone. In some embodiments, the support ring 42 comprises a substantially constant strut width, and in some embodiments, struts of the support ring 42 have a greater width than elements of the serpentine bands 20 or other side branch structure 60. In some embodiments, the struts of the support ring 42 have an average width that is greater than an average width of the struts 80 of the first side branch ring 70.

In some embodiments, the support ring 42 extends continuously around the side branch structure 60. In some embodiments, the support ring 42 comprises a structure that is continuously concave with respect to the side branch center point 68. Thus, in some embodiments, the support ring 42 does not include any portions of curvature that are convex with respect to the side branch center point 68.

In some embodiments, the support ring 42 includes a first portion 82 and a second portion 84 located on axially opposed sides of the side branch structure 60. In some embodiments, the second portion 84 comprises a mirror image of the first portion taken across the side branch minor axis, which can be oriented in a stent circumferential direction and can pass through the side branch center point 68. In some embodiments, at least a portion of either portion 82, 84 can comprise a parabolic shape that is concave with respect to the side branch center point 68.

Figure 3:
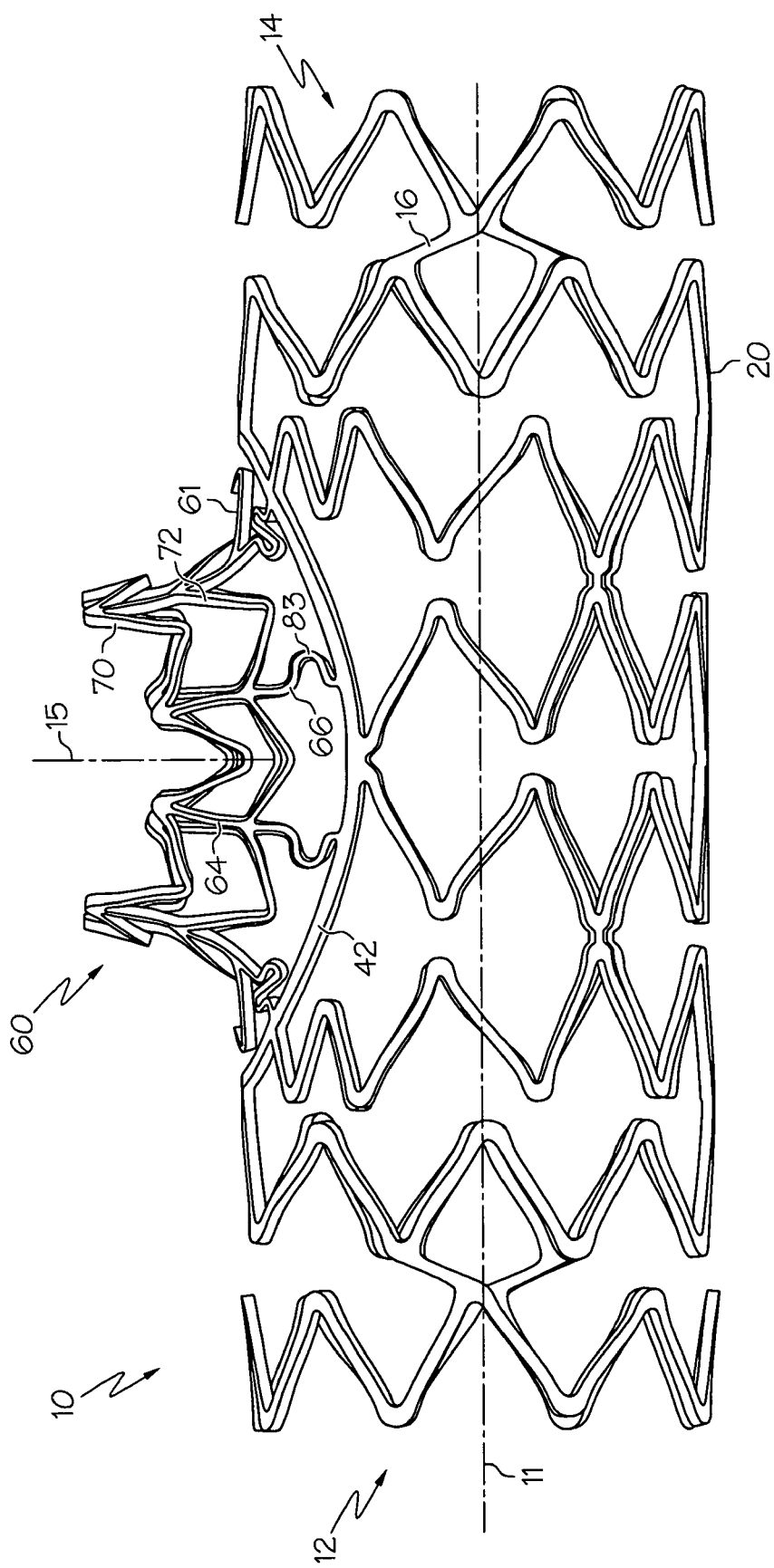
FIG. 3 shows a side view of a stent according to the flat pattern of FIG. 1 in an expanded state.

FIG. 3 shows a side view of a stent according to the flat pattern of FIG. 1. The stent 10 is shown in an expanded configuration with the side branch structure 60 outwardly deployed.

The serpentine bands 20 form a generally cylindrical stent body structure that extends around the stent longitudinal axis 11. The side branch structure 60 extends in a radial outward direction above the generally cylindrical stent body structure. Portions of the outwardly deployed side branch structure 60 are located farther away from the stent longitudinal axis 11 than portions of the stent 10 that form the generally cylindrical stent body structure.

The outwardly deployed side branch rings 70, 72 form a tubular structure having a side branch axis 15 that is nonparallel to the stent longitudinal axis 11. In some embodiments, the side branch axis 15 is orthogonal to the stent longitudinal axis 11.

The side branch outer connectors 66 have each deformed to allow the side branch structure 60 to deploy radially outwardly. The shape of the side branch outer connectors 66, for example the turns 83, helps to allow for flexibility and bending.

In some embodiments, the ancillary side branch structure 61 remains substantially aligned with the generally cylindrical stent body structure after deployment of the side branch structure 60. Therefore, while the side branch structure 60 would extend into a side branch vessel when deployed at a vessel bifurcation, the ancillary side branch structure 61 can remain within the main vessel and can provide support to the bifurcation, such as the carina.

Figure 4:
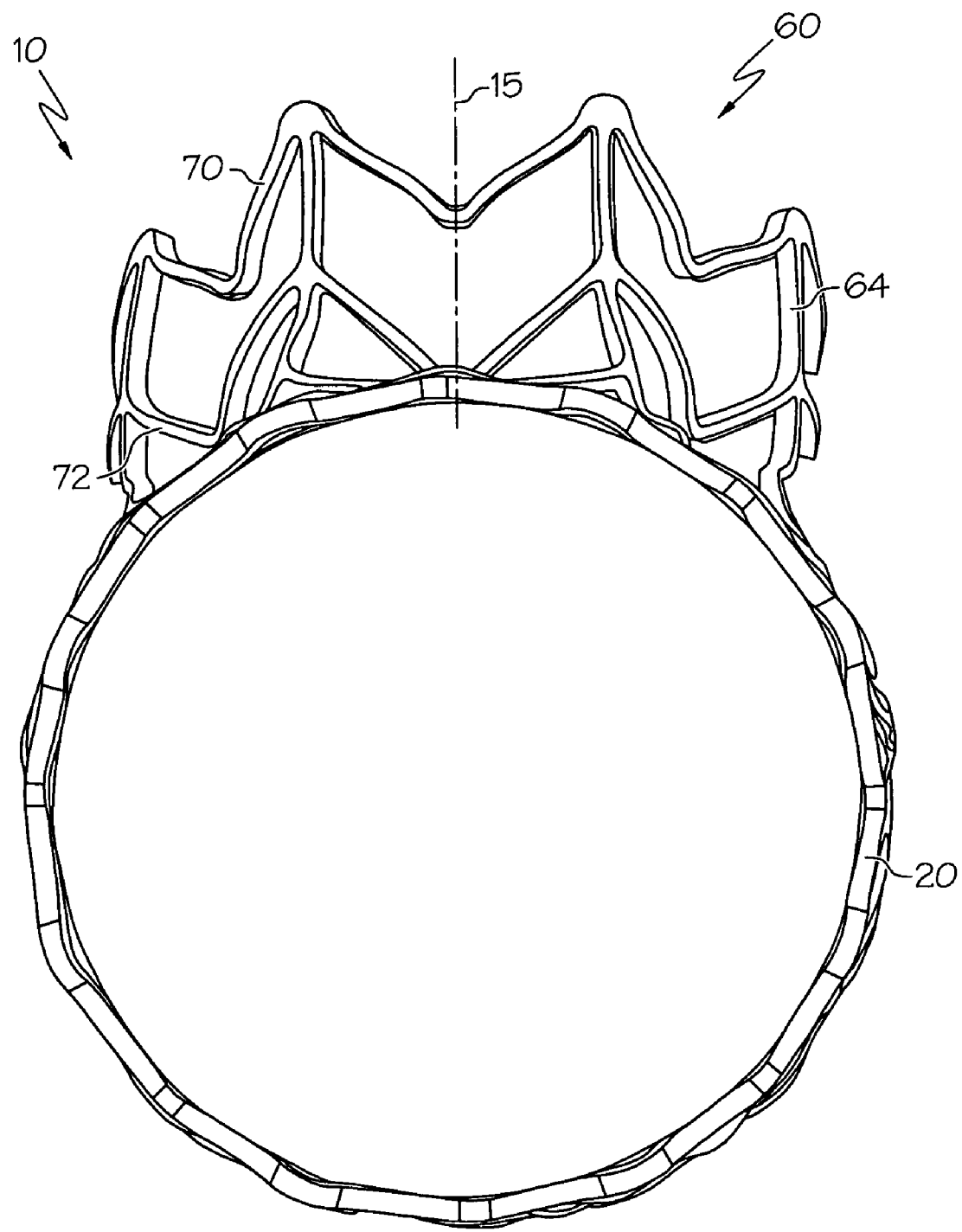
FIG. 4 shows an end view of a stent according to the flat pattern of FIG. 1 in an expanded state.

FIG. 4 shows an end view of a stent according to the flat pattern of FIG. 1 in an expanded state.

Figure 5:
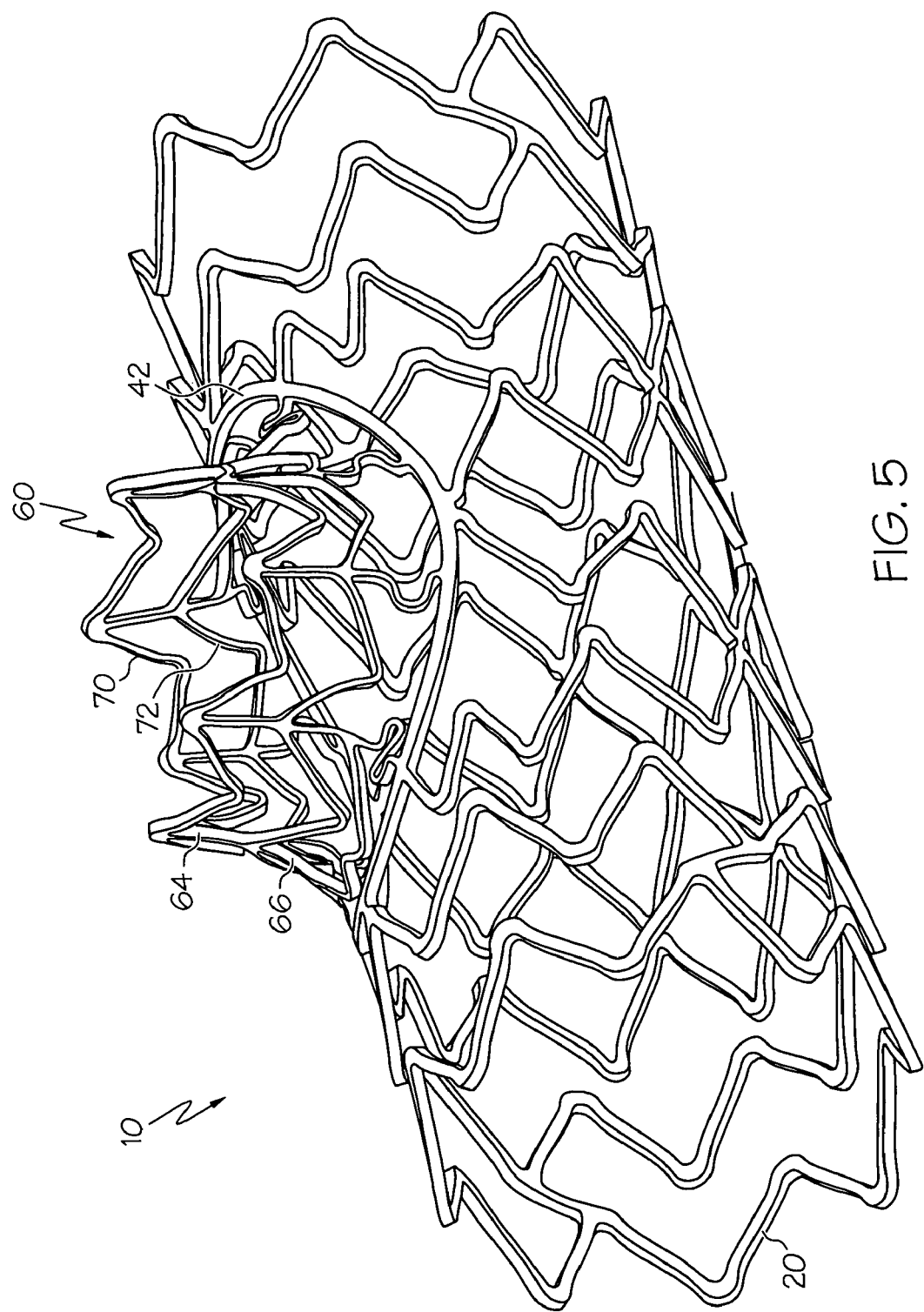
FIG. 5 shows an isometric view of a stent according to the flat pattern of FIG. 1 in an expanded state.

FIG. 5 shows a three-dimensional view of a stent according to the flat pattern of FIG. 1 in an expanded state.

Figure 6:
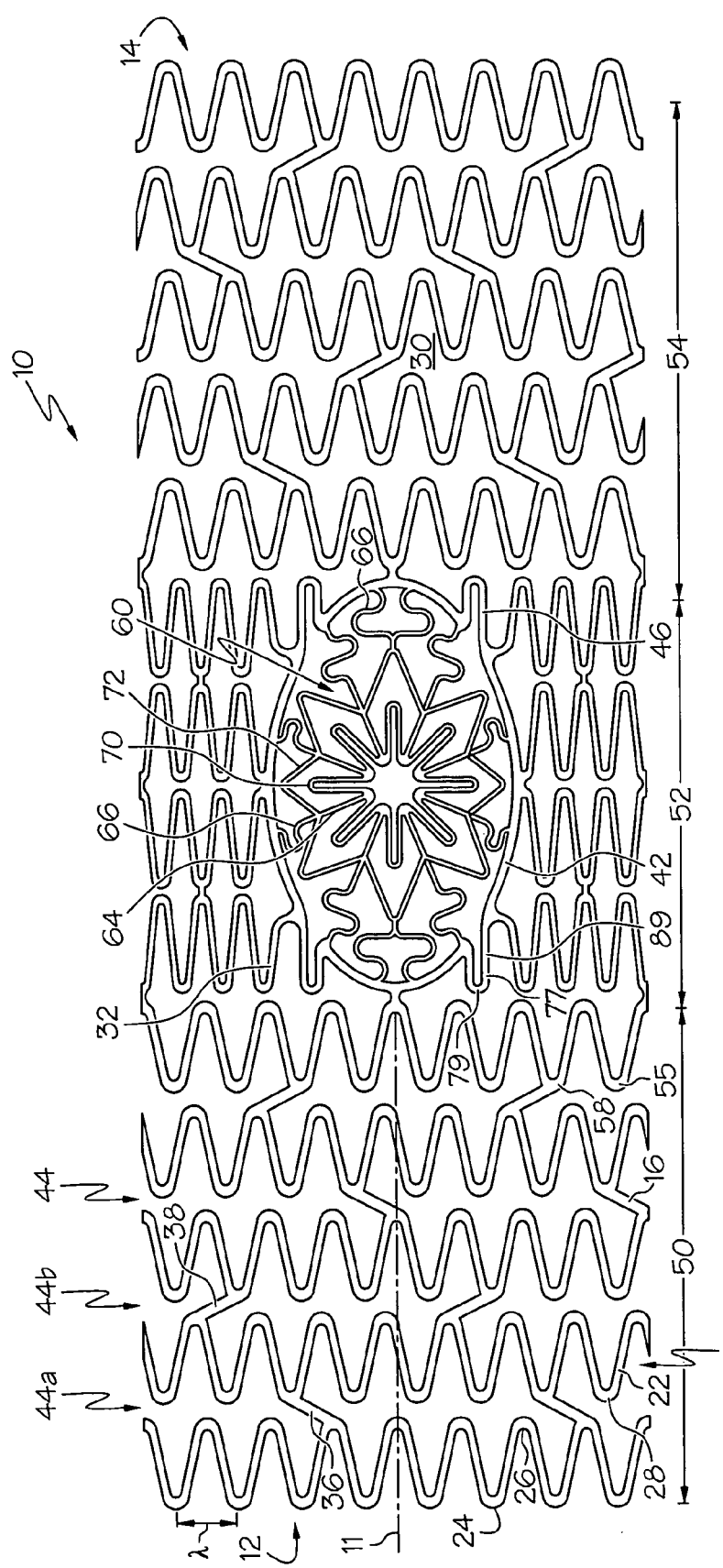
FIG. 6 shows a flat pattern for another embodiment of a stent.

FIG. 6 shows a flat pattern for another embodiment of a stent.

In some embodiments, a side branch outer connector 66 can be connected to the support ring 42 at two locations, and can also be connected to the second serpentine ring 72.

In some embodiments, the support ring 42 comprises at least one straight portion 46. In some embodiments, a straight portion 46 is oriented parallel to the stent longitudinal axis 11.

In some embodiments, the support ring 42 comprises one or more loop portions 77. In some embodiments, a loop portion 77 comprises a loop turn 79 and one or more loop struts 89. In some embodiments, a loop strut 89 is straight along its length. In some embodiments, a loop strut 89 is oriented parallel to the stent longitudinal axis 11. In some embodiments, a loop turn 79 is oriented with a peak (e.g. a maximum or minimum) oriented in a stent longitudinal direction. Thus, the loop turn 79 can be bisected by a line that is parallel to the stent longitudinal axis 11. This configuration of loop portions 77 allows the support ring 42 to expand in the stent circumferential direction with lessened longitudinal shortening of the support ring 42 than if the support ring 42 did not include loop portions 77. This configuration can also help to provide apposition between the support ring 42 and areas of a vessel bifurcation, such as an elliptical intersection ring between a primary vessel and a branch vessel, while the support ring 42 remains within the primary vessel.

In some embodiments, one loop portion 77 can comprise a mirror image of another loop portion 77 taken across a stent longitudinal axis that intersects the side branch center point 68. A loop portion 77 can also comprise a mirror image of another loop portion 77 taken across an axis oriented in the stent circumferential direction that passes through the side branch center point 68.

Figure 7:
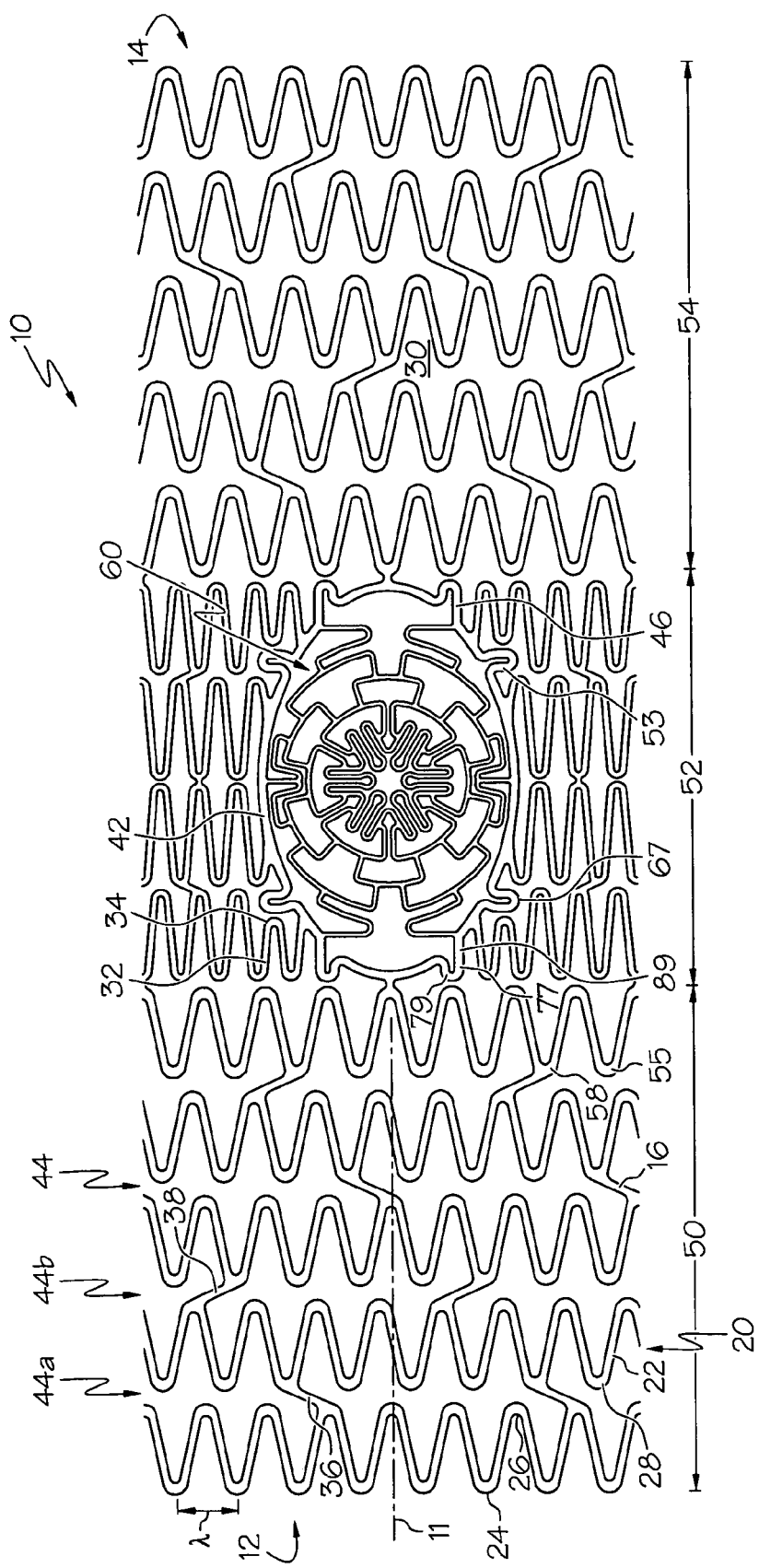
FIG. 7 shows a flat pattern for another embodiment of a stent.

FIG. 7 shows a flat pattern for another embodiment of a stent.

In some embodiments, the support ring 42 comprises at least one first straight portion 46 and at least one second straight portion 53. In some embodiments, a first straight portion 46 is oriented parallel to the stent longitudinal axis 11. In some embodiments, a first straight portion 46 is oriented perpendicular to a second straight portion 53.

In some embodiments, the support ring 42 comprises one or more first loop portions 77 and one or more second loop portions 67. In some embodiments, a second loop portion 67 comprises a loop turn 79 and one or more loop struts 89. In some embodiments, a loop strut 89 is straight along its length. In some embodiments, a loop strut 89 is oriented perpendicular to the stent longitudinal axis 11. In some embodiments, a loop turn 79 is oriented with a peak (e.g. a maximum or minimum) oriented perpendicular to a stent longitudinal direction. Thus, the loop turn 79 can be bisected by a line that is perpendicular to the stent longitudinal axis 11.

In some embodiments, a loop strut 89 of a first loop portion 77 is oriented perpendicular to a loop strut 89 of a second loop portion 67.

Figure 8:
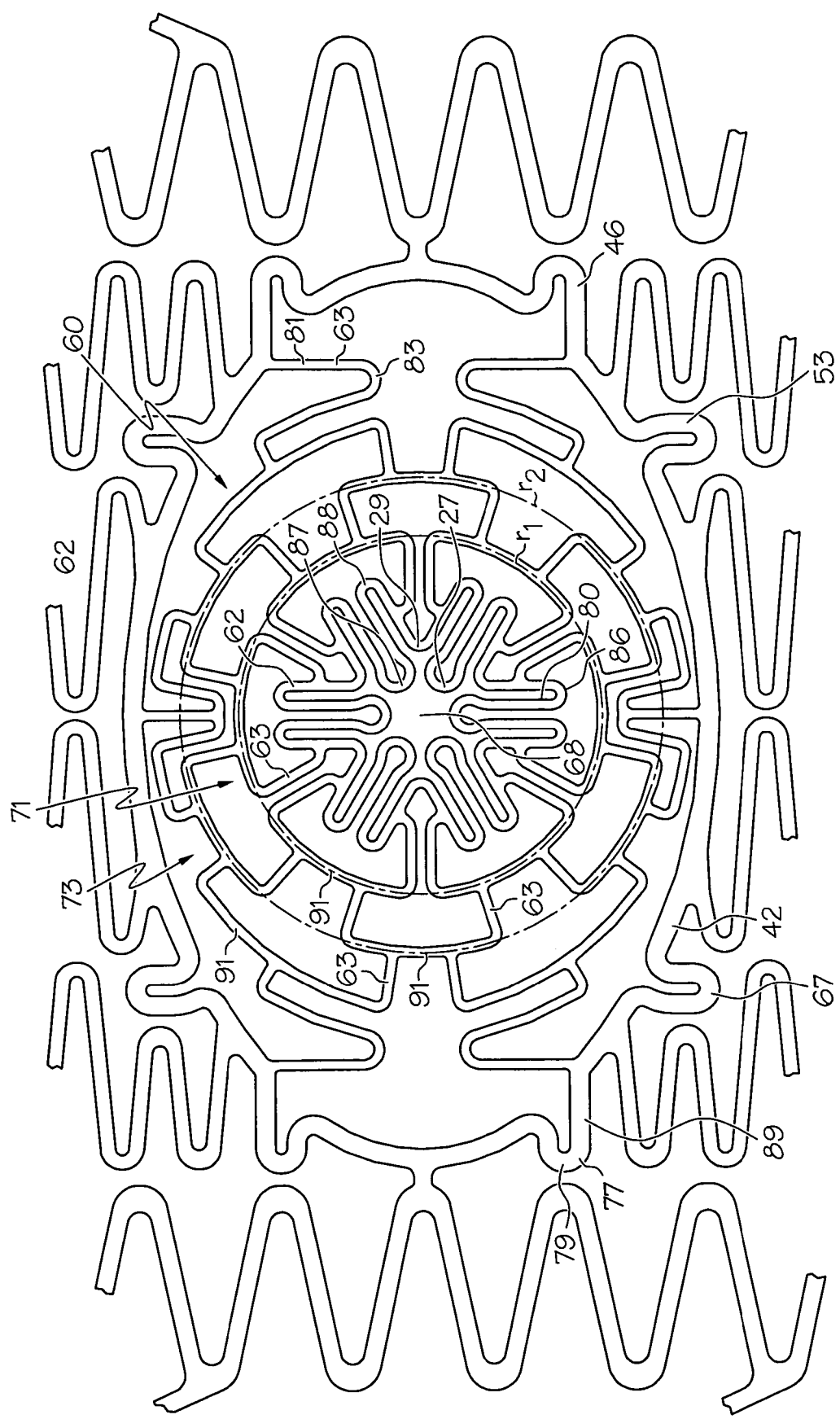
FIG. 8 shows a portion of FIG. 7 in greater detail.

FIG. 8 shows a portion of FIG. 7 in greater detail. In some embodiments, the side branch structure 60 comprises a serpentine ring 62, a plurality of arcuate struts 91 and a plurality of side branch connectors 63.

In some embodiments, a serpentine ring 62 comprises a plurality of alternating struts 80 and turns 86. The turns 86 can comprise alternating inner turns 87 and outer turns 88. The inner turns 87 are generally located closer to the side branch center point 68 than the outer turns 88. In some embodiments, inner turns 87 point inward with respect to the side branch, for example pointing toward the side branch center point 68. In some embodiments, outer turns 88 point outward with respect to the side branch, for example pointing away from the side branch center point 68.

In some embodiments, the inner turns 87 can further comprise alternating first inner turns 27 and second inner turns 29. The first inner turns 27 are generally located closer to the side branch center point 68 than the second inner turns 29. In some embodiments, the first inner turns 27 are each located an equal distance away from the side branch center point 68, and thus can be considered aligned around a reference circle (not shown). In some embodiments, the second inner turns 29 are each located an equal distance away from the side branch center point 68, and thus can be considered aligned around another reference circle (not shown).

In some embodiments, a first inner turn 27 comprises a greater arc length than a second inner turn 29. In some embodiments, a central angle of a first inner turn 27 can be greater than 180 degrees. In some embodiments, a central angle of a second inner turn 29 can be less than 180 degrees.

In some embodiments, each strut 80 of the side branch ring 62 is straight along its length. In some embodiments, a strut 80 that connects between a first inner turns 27 and an outer turn 88 can be longer than a strut 80 that connects between a second inner turn 29 and an outer turn 88. In some embodiments, a side branch ring 62 comprises four consecutive struts 80 that are parallel to one another.

In some embodiments, the side branch structure 60 comprises a plurality of arcuate struts 91. An arcuate strut 91 includes curvature along its length. In some embodiments, an arcuate strut 91 is concave with respect to the side branch center point 68. In some embodiments, each arcuate strut 91 included in the side branch structure 60 is concave with respect to the side branch center point 68.

In some embodiments, the side branch structure 60 comprises a first plurality 71 of arcuate struts 91 that are aligned around a first reference circle $r_1$, which can be centered upon the side branch center point 68. In some embodiments, the first plurality 71 of arcuate struts 91 collectively comprises at least half of a circumference of the first reference circle $r_1$. In some embodiments, the first plurality 71 of arcuate struts 91 collectively comprises at least three-fourths of the circumference of the first reference circle $r_1$.

In some embodiments, the side branch structure 60 further comprises a second plurality 73 of arcuate struts 91 that are aligned around a second reference circle $r_2$, which can be centered upon the side branch center point 68. In some embodiments, the second plurality 73 of arcuate struts 91 collectively comprises at least half of a circumference of the second reference circle $r_2$. In some embodiments, the second reference circle $r_2$ is larger than the first reference circle $r_1$.

In some embodiments, a side branch connector 63 can be oriented substantially in a side branch radial direction. In some embodiments, a side branch connector 63 connects between a strut 80 of a side branch ring 62 and an arcuate strut 91 included in the first plurality 71. In some embodiments, a side branch connector 63 connects between a middle portion of a strut 80 of a side branch ring 62 and an end of an arcuate strut 91 included in the first plurality 71. In some embodiments, a side branch connector 63 connects between an arcuate strut 91 included in the first plurality 71 and an arcuate strut 91 included in the second plurality 73. In some embodiments, a side branch connector 63 connects between a central portion of an arcuate strut 91 included in the first plurality 71 and an end of arcuate strut 91 included in the second plurality 73. In some embodiments, a side branch connector 63 connects between an arcuate strut 91 included in the second plurality 73 and another arcuate strut 91, such as an arcuate strut 91 that is not included in either plurality 71, 73.

In some embodiments, a side branch connector 63 comprises at least one straight portion 81 and at least one bent portion 83. In some embodiments, a side branch connector 63 connects between an arcuate strut 91 and the support ring 42.

Figure 9:
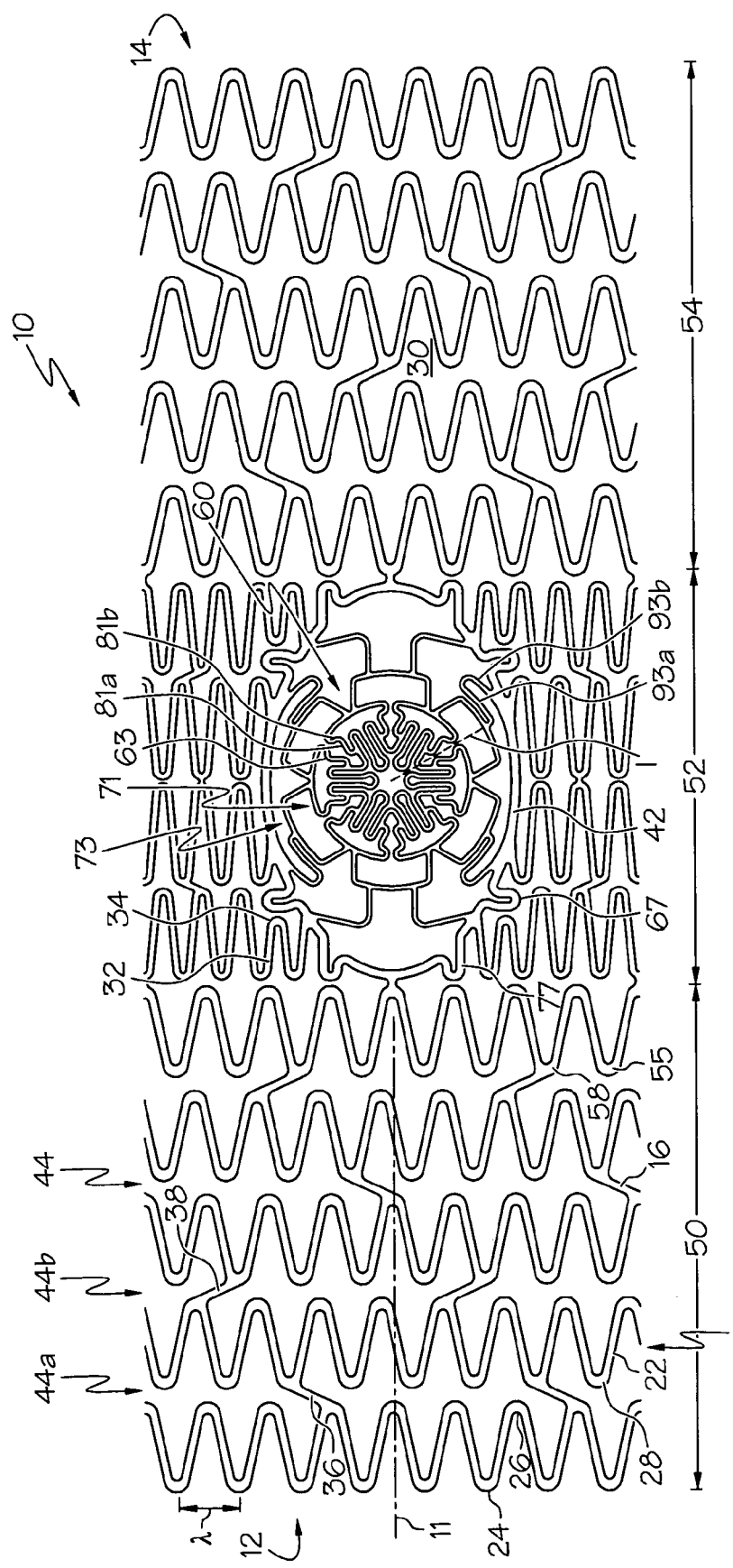
FIG. 9 shows a flat pattern for another embodiment of a stent.

FIG. 9 shows a flat pattern for another embodiment of a stent. The pattern is similar to the patter shown in FIG. 7, as indicated by like reference characters.

In some embodiments, a side branch connector 63 comprises a first straight portion 81a and a second straight portion 81b. In some embodiments, the first straight portion 81a is perpendicular to the second straight portion 81b.

In some embodiments, the side branch connectors 63 that connect to either end of an arcuate strut 91 can be parallel to one another. In some embodiments, the side branch connectors 63 can also be parallel to a reference line l oriented in a side branch radial direction that bisects the arcuate strut 91.

In some embodiments, a side branch connector 63 comprises a first curved portion 93a and a second curved portion 93b. In some embodiments, the first curved portion 93a is parallel to and offset from the second curved portion 93b.

Figure 10:
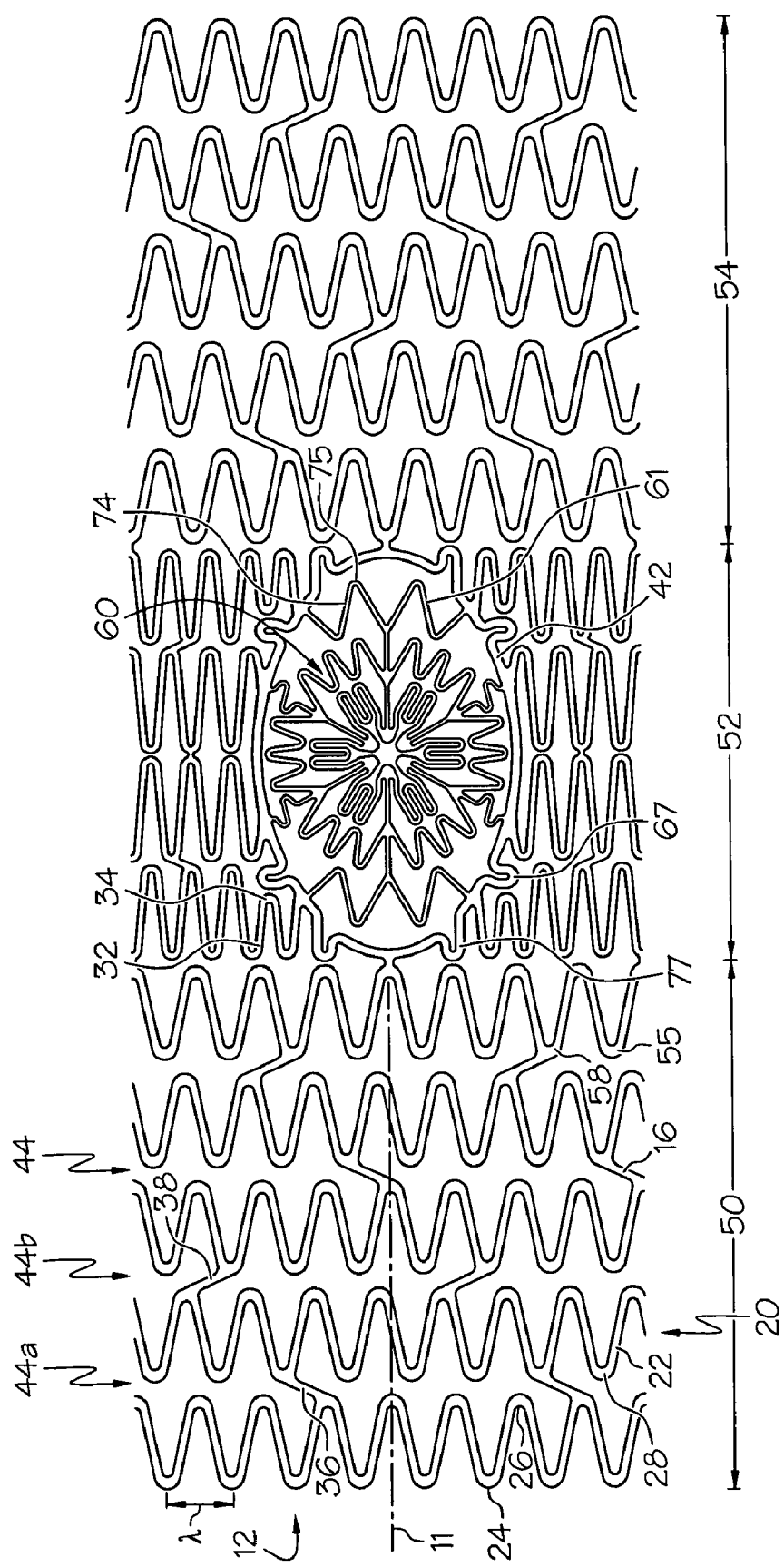
FIG. 10 shows a flat pattern for another embodiment of a stent.
Figure 11:
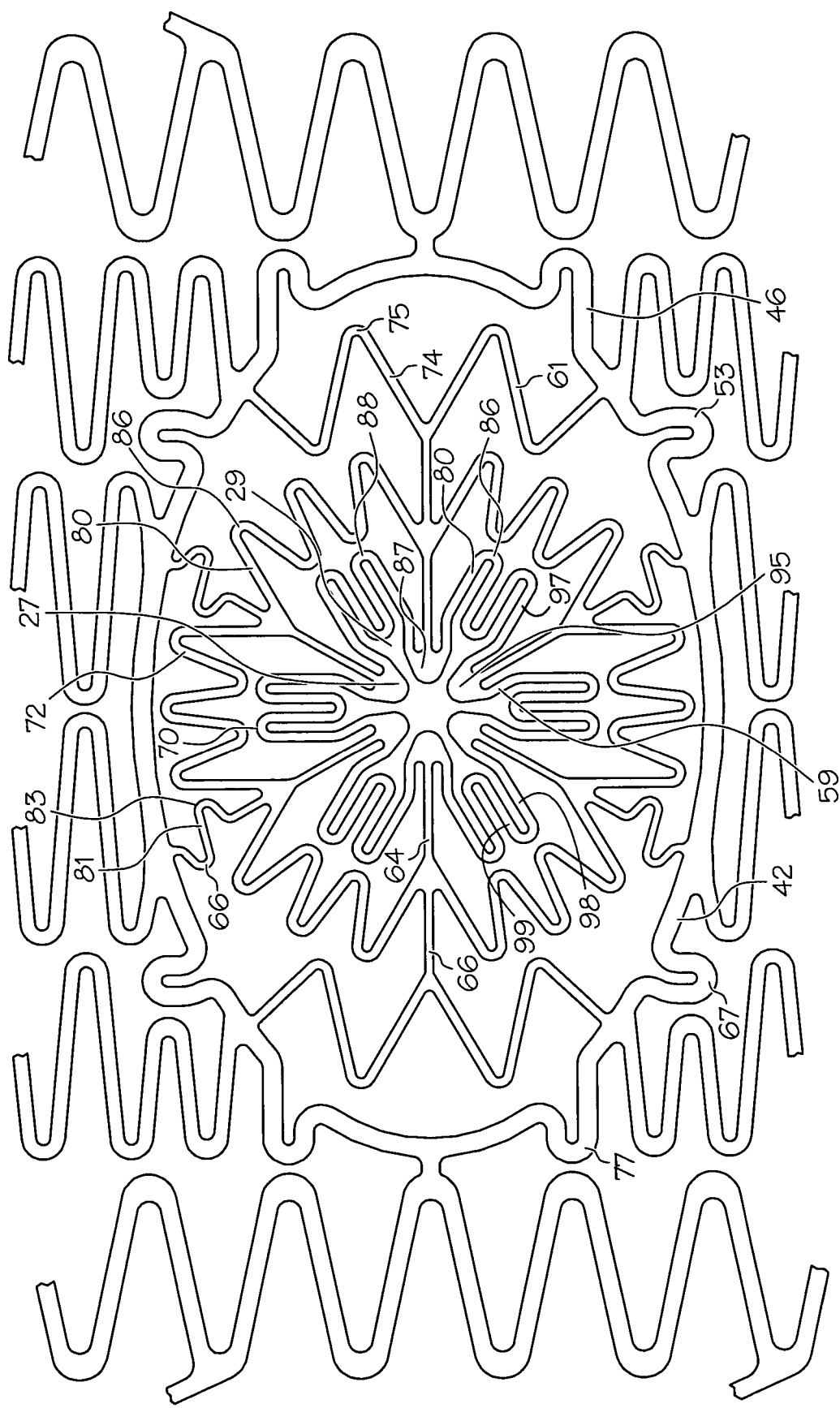
FIG. 11 shows a portion of FIG. 10 in greater detail.

FIG. 10 shows a flat pattern for another embodiment of a stent 10. FIG. 11 shows a portion of FIG. 10 in greater detail.

In some embodiments, the first side branch ring 70 comprises alternating petals 95 and linking members 97. Each petal 95 comprises an inner turn 87. In some embodiments, each petal can further comprise one or more strut portions 59. Each linking member 97 comprises a plurality of struts 80 and at least one turn 86. In some embodiments, all of the struts 80 of a linking member 97 are parallel to one another. In some embodiments, a linking member 97 comprises a plurality of struts 80 and a plurality of turns 86. In some embodiments, a linking member 97 comprises a plurality of outer turns 88 and at least one inner turn 87. In some embodiments, each inner turn 87 that is a portion of a petal 95 comprises a first inner turn 27, and each inner turn 87 that is a portion of a linking member 97 comprises a second inner turn 29.

The first side branch ring 70 shown in FIG. 11 can also be described as comprising alternating struts 80 and turns 86. The turns 86 can comprise alternating inner turns 87 and outer turns 88. The inner turns 87 can comprise alternating first inner turns 27 and second inner turns 29. The first inner turns 27 can be located closer to the side branch center point 68 than the second inner turns 29. The struts 80 can comprise straight struts 99 and bent struts 98. In some embodiments, the first side branch ring 70 comprises a repeating pattern of two adjacent straight struts 99 and two adjacent bent struts 98 as the first side branch ring 70 is traversed. The adjacent straight struts 99 can be parallel to one another. The adjacent bent struts 98 can comprise mirror images of one another taken across a line extending in a side branch radial direction. A straight strut 99 can connect between an outer turn 88 and a second inner turn 29. A bent strut 98 can connect between an outer turn 88 and a first inner turn 27.

In some embodiments, the second side branch ring 72 comprises alternating struts 80 and turns 86. In some embodiments, second side branch ring 72 comprises more struts 80 and more turns 86 than the first side branch ring 70. In some embodiments, second side branch ring 72 comprises 1.5 times as many struts 80 and 1.5 times as many turns 86 as the first side branch ring 70.

In some embodiments, a side branch inner connector 64 is oriented in a side branch radial direction. In some embodiments, a side branch inner connector 64 connects between a petal 95 of the first side branch ring 70 and an inner turn 87 of the second side branch ring 72.

In some embodiments, the ancillary side branch structure 61 comprises a plurality of ancillary struts 74 and ancillary turns 75. In some embodiments, the ancillary side branch structure 61 connects to the support ring 42 at one or more locations. In some embodiments, an outer side branch connector 66 connects between the second side branch ring 72 and the ancillary side branch structure 61. In some embodiments, an outer side branch connector is attached to an ancillary turn 75.

Figure 12:
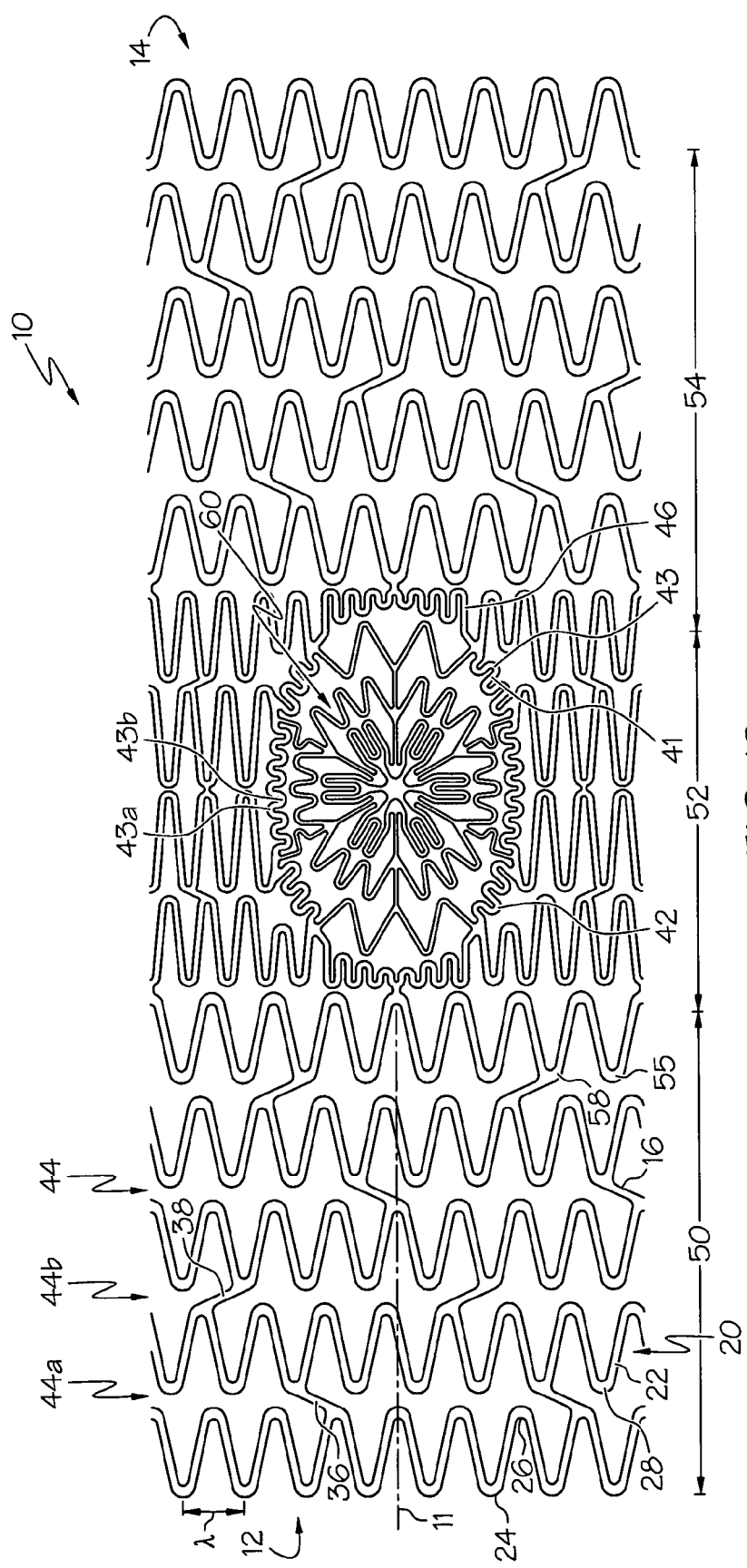
FIG. 12 shows a flat pattern for another embodiment of a stent.

FIG. 12 shows a flat pattern for another embodiment of a stent 10. Many portions of the side branch structure 60 are similar to portions of the side branch structure 60 shown in FIG. 10.

In some embodiments, the support ring 42 comprises a plurality of struts 41 and a plurality of turns 43. In some embodiments, a plurality of adjacent struts 41 are all parallel to one another. In some embodiments, the support ring 42 comprises a plurality of struts 46 oriented parallel to the stent longitudinal axis 11.

In some embodiments, a section of the support ring 42 comprises a plurality of connected alternating first turns 43a and second turns 43b. The first turns 43a and second turns 43b can comprise different orientations of curvature. For example, if a first turn 43a can be considered concave with respect to the side branch center point 68, a second turn 43b can be considered convex with respect to the side branch center point 68. The transition from a first turn 43a to a second turn 43b can comprise an inflection.

In some embodiments, a stent can be described according to the following numbered paragraphs.

1) A stent comprising:
 a plurality of interconnected framework members defining a plurality of cells, a portion of the interconnected framework members comprising a side branch structure defining an inner side branch cell, the inner side branch cell being shaped differently than other cells of the stent;
 the side branch structure comprising:
  a first serpentine ring extending around the inner side branch cell, the first serpentine ring comprising alternating petals and linking members, each linking member comprising a plurality of parallel struts connected by turns.
2) The stent of paragraph 1, the side branch structure further comprising a second serpentine ring extending around the first serpentine ring, and a plurality of inner side branch connectors, each inner side branch connector connecting between a petal and the second side branch ring.
3) The stent of paragraph 2, wherein each inner side branch connector extends in a side branch radial direction.
4) The stent of paragraph 2, wherein each linking member comprises three turns.
5) The stent of paragraph 4, wherein the second serpentine ring comprises alternating struts and turns.
6) The stent of paragraph 5, wherein the second serpentine ring comprises more turns than the first serpentine ring.
7) The stent of paragraph 6, wherein each petal comprises a turn.
8) The stent of paragraph 1, further comprising a continuous support ring extending around the side branch structure.
9) The stent of paragraph 8, the support ring comprising a plurality of loops.
10) The stent of paragraph 9, wherein a loop comprises a loop turn that extends 180 degrees.
11) The stent of paragraph 10, comprising a first loop turn centered in a stent axial direction.
12) The stent of paragraph 11, comprising a second loop turn centered in a stent circumferential direction.

The inventive stents can be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents can be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents can be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly can include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent comprising:
a plurality of interconnected framework members defining a plurality of cells, a portion of the interconnected framework members comprising a side branch structure defining an inner side branch cell, the inner side branch cell being shaped differently than other cells of the stent, a portion of the interconnected framework members comprising a support ring extending continuously around the side branch structure, the support ring being continuously concave with respect to a side branch center point;
the side branch structure comprising:
a first serpentine ring extending around and defining the inner side branch cell, the first serpentine ring comprising alternating inner turns and outer turns connected by straight struts, the inner turns being distributed around a reference circle centered upon the side branch center point;
a second serpentine ring extending around the first serpentine ring, the second serpentine ring comprising alternating inner turns and outer turns connected by straight struts, the second serpentine ring having the same number of inner turns and outer turns as the first serpentine ring;
a plurality of inner side branch connectors, each inner side branch connector spanning between the first serpentine ring and the second serpentine ring in a side branch radial direction;
a plurality of outer side branch connectors, each outer side branch connector spanning between the second serpentine ring and the support ring, each outer side branch connector comprising a curved portion, at least some of the outer side branch connectors comprising an s-shape; and
an ancillary side branch structure strut attached at one end to a said outer side branch connector having said s-shape and attached at another end to another said outer side branch connector having said s-shape;
wherein said support ring is separate and distinct from said side branch structure.

2. The stent of claim 1, wherein each inner side branch connector spans between an inner turn of the first serpentine ring and an inner turn of the second serpentine ring.

3. The stent of claim 1, wherein each outer turn of the first serpentine ring is aligned with an outer turn of the second serpentine ring in a side branch radial direction.

4. The stent of claim 1, the support ring comprising an average strut width greater than an average strut width of the first serpentine ring.

5. The stent of claim 4, wherein the support ring is elliptical.

6. The stent of claim 4, each outer side branch connector spanning between an inner turn of the second side branch ring and the support ring.

7. The stent of claim 1, wherein the first serpentine ring comprises a plurality of strut pairs, the struts of a strut pair being parallel to one another and connected by an outer turn.

8. The stent of claim 1, wherein a plurality of said outer side branch connectors each comprises a first elongate straight portion oriented perpendicular to a second elongate straight portion.

9. The stent of claim 8, further comprising a second ancillary side branch structure strut connected between two outer side branch connectors.

10. The stent of claim 8, wherein said first elongate straight portion is oriented in a side branch radial direction.

11. The stent of claim 1, wherein the side branch structure comprises a proximal half and a distal half, the proximal half shaped according to a reflection of the distal half taken across a bisecting axis oriented in a stent circumferential direction.

12. The stent of claim 1, wherein said ancillary side branch structure is connected only to said outer side branch connectors.

13. The stent of claim 1, wherein said ancillary side branch structure is connected to said outer side branch connectors at a location between the s-shape and the second serpentine ring.

14. The stent of claim 1, wherein said ancillary side branch structure comprises a w-shape.

* * * * *